United States Patent [19]
Zeitels

[11] Patent Number: 5,893,830
[45] Date of Patent: Apr. 13, 1999

[54] UNIVERSAL MODULAR LARYNGOSCOPE/ GLOTTISCOPE SYSTEM

[76] Inventor: Steven Zeitels, 166 Beacon St., #3, Boston, Mass. 02116

[21] Appl. No.: 09/104,182

[22] Filed: Jun. 25, 1998

[51] Int. Cl.$^6$ ................................................ A61B 1/26
[52] U.S. Cl. ........................ 600/190; 600/185; 600/208
[58] Field of Search ................................ 600/185, 187, 600/188, 190, 193, 197, 201, 208, 235, 237

[56] References Cited

U.S. PATENT DOCUMENTS

| | | |
|---|---|---|
| 4,337,761 | 7/1982 | Upsher . |
| 4,799,485 | 1/1989 | Furey et al. . |
| 4,832,004 | 5/1989 | Heckele . |
| 4,947,829 | 8/1990 | Bullard . |
| 4,958,624 | 9/1990 | Stone et al. . |
| 5,092,314 | 3/1992 | Zeitels . |
| 5,261,392 | 11/1993 | Wu . |

OTHER PUBLICATIONS

Steven M. Zeitels and Charles W. Vaughan, "'External Counterpressure' and 'Internal Distention' for Optimal laryngoscopic Exposure of the Anterior Glottal Commissure",*Annals of Otology, Rhinology & Laryngology*, vol. 103, No. 9, Sep. 1994.

H. Weerda, "A New Distending Laryngoscope for Diagnoscope and Microsurgery of the Larynx", *Laryngoscope*, May 1983.

"Richard Wolf's Exclusive Anterior Commissure Laryngoscope", Richard Wolf Medical Instruments Corp.

"Distending Operating Laryngoscope", Karl Storz GmbH & Company.

"Adjustable Laryngo–Pharyngoscope", Richard Wolf Medical Instruments Corp.

"Lindholm Laryngoscope", Storz.

"Laryngoscopes/Tracheascopes", Pilling Endoscopic Instruments, p. 16.

"Micro–Laryngoscopes and Instrumentation", Pilling Endoscopic Instruments, p. 21.

"Laryngoscope Holders", Pilling Endoscopic Instruments, p. 41.

"Laryngoscope Holders", Pilling Endoscopic Instruments, p. 40.

"Laryngeal Instrumentation", Pilling Endoscopic Instruments, p. 44.

*Primary Examiner*—Beverly M. Flanagan
*Attorney, Agent, or Firm*—McDermott, Will & Emery

[57] ABSTRACT

A universal modular glottiscope system includes a set of differently dimensioned elongate tubular elements for insertion into a patient's larynx for laryngoscopic procedures or intubation. Each tubular element has a substantially triangular cross-section distally defined by a substantially planar base and two curved sides which intersect at an apex line and may have varying curvature between the apex line and the base. A distal end opening is defined by an intersection of the cross-section with an imaginary plane at a selected angle to the longitudinal direction of the tubular element. At the proximal end of each tubular element, which is D-shaped in configuration and wider than the distal end, is provided a pair of opposed end slots intermediate the apex line and the base. The planar base is detachable. Above the slots, adjacent the proximal end of each tubular element, is a standardized handle-attachment fitting. A surgeon using the system may inspect the patient and, based on measurements and/or experience, select the most suitable elongate tubular element from the set and manually attach a standardized handle element thereto at the standardized handle-attachment thereof.

27 Claims, 4 Drawing Sheets

UNIVERSAL MODULAR LARYNGOSCOPE/ GLOTTISCOPE SYSTEM

TECHNICAL FIELD

This invention relates to a universal glottiscope system which enables a surgeon to perform laryngoscopic procedures on patients of differing anatomy. More particularly, it relates to a novel modular laryngoscope/glottiscope system in which a suspension handle may be selectively assembled and operatively attached to any one of a set of elongate tubular or spatula elements of different sizes.

BACKGROUND ART

Instruments generally known as laryngoscopes are routinely used to facilitate endotracheal intubation of patients, e.g., to provide a temporary air passage for administration of anesthetic substance or to overcome an obstruction of the air passage to a patient's lungs. Laryngoscopes, in various forms, are also commonly used in surgery to displace oral cavity and pharyngeal tissues to enable a surgeon to perform direct inspection and surgical manipulation of a patient's larynx, a procedure known as direct laryngoscopy. The typical laryngoscope has an elongate portion, which may be of adjustable geometry, that is introduced through the patient's mouth into the larynx. An attached handle enables the surgeon to manipulate not only the portion introduced into the patient's larynx but, as appropriate, to position the distal end of the inserted element to perform inspection and/or surgical operations. One or more surgical tools may be inserted simultaneously via the inserted element. Otolaryngologists typically use a laryngoscope having a tubular portion insertable into the patient's larynx to the glottis, i.e., the true vocal cords or folds, both for viewing and for endoscopic surgical operations thereon.

The surgeon must have a clear view of the affected tissue and must be able to perform precise surgery, sometimes with more than one tool utilized simultaneously. Because of the limited dimensions of the human oral cavity, pharynx and larynx, and the inevitable discomfort suffered by the patient in such a procedure, it is extremely important to enable the surgeon to have the widest access and maximum freedom for manipulating necessary instrumentation, and to reduce the time during which physical invasion of the patient's larynx must occur.

Particularly for patients who need to improve or maintain their voices, specialized surgery known as phonomicrosurgery is performed with the use of a surgical microscope. Such phonomicrosurgery is optimized by obtaining the widest glottal surgical field to expose vocal-fold anomalies such as polyps, nodules, cysts, granulomas, papilloma, epithelial dysplasia, and cancerous growths.

The human vocal folds (glottis) comprise an approximately isosceles-triangle-shaped valve that is fixed anteriorly and opens and closes posteriorly to allow for respiration and phonation, respectively. Lesions of the vocal folds may occur in patients of all ages and of both genders. A clear human voice is predicated on aerodynamically-driven, symmetrically-entrained oscillation of the vocal folds. When the vocal folds are closed during phonation, the expired air stream from the trachea is opposed by the closed glottal valve. Under sustained aerodynamic pressure, the vocal folds will vibrate to generate phonation. This vibration becomes disordered, and hoarseness develops, if there is a lesion on the vocal folds. Most benign lesions of the vocal folds, except lesions caused by viral infection, tend to develop in vocal over-users.

Successful phonomicrosurgery depends on maximal preservation of the layered microstructure of the healthy vocal fold tissue and is facilitated by the largest appropriately-shaped laryngoscope that can be placed between the patient's lips and glottis. Accordingly, the optimal laryngoscope will be one which facilitates ideal exposure of the pathology and, in turn, hand-instrument examination and retraction of the lesion for examination and resection.

In the known prior art, the problem of effectively angulating hand-held and operated instruments within the lumen of the laryngoscope element inserted into the patient's mouth and larynx was solved in two ways: by forming the lumen structure to have a widened proximal aperture of a tubular laryngoscope or, in the alternative, by using a bivalved spatula laryngoscope comprised of two pivotably separable distending spatula blades. The latter tends to be unstable distally away from the distending mechanism. A single slot was sometimes provided in the lumen to facilitate manipulation of proximal end portions of surgical instruments therein, but this provided room for instrument manipulation on only one side of the laryngoscope. The prior art furthermore suffers from an inability to provide the dimensional versatility required when treating patients of differing anatomy.

A need exists for a modular glottiscope system which enables a surgeon to treat patients of different sizes, permits access to specific portions of the larynx with greater precision and comfort for the patient, and permits flexibility in manipulation of one or more viewing and/or surgical tools and, because of its modular variations, easily adapts for intubation applications. The present invention is intended to meet all of these needs.

DISCLOSURE OF THE INVENTION

Accordingly, in a first aspect of this invention, there is provided a novel universal modular glottiscope system, which includes a plurality of elongate tubular elements of different counterpart dimensions, respectively, each element having a distal end to be inserted into a patient's larynx and a proximal end through which one or more surgical devices may be inserted operatively by the surgeon. An aperture is defined internally by the wall of the tubular element. The distal portion of each tubular element is of generally triangular cross-section, having a substantially planar base that, in a preferred embodiment, is detachable, and a pair of curved sides that intersect above the base. Preferably, the proximal portion is D-shaped in cross section with a top that is generally ovoid in configuration, and sides provided with respective slots of predetermined width and length, located intermediate of he tubular element. The aperture of the tubular element at the proximal portion preferably is slightly wider than at the distal end, to accommodate to the optical requirements of a surgical microscope.

The tubular elements are provided in a variety of sizes to facilitate choice by the surgeon of the most appropriate one for a particular patient and a particular surgical operation. A standardized handle-attachment member is affixed to the proximal end of each of the tubular elements, and the system includes a handle manually attachable to and detachable from the standardized handle-attachment member of any of the elongate tubular elements.

In another preferred embodiment of the apparatus, there is provided an improved laryngoscope comprising an elongate tubular element having a distal end to be inserted into a patient's larynx and a proximal end through which one or more surgical devices may be inserted individually or simultaneously, the system having a handle attachable to a proximal end portion of the tubular element. The distal portion of the tubular element is configured with a generally triangular cross-section defined by a substantially planar base of a predetermined length and a pair of curved sides which intersect at a predetermined first angle at an apex line located at a predetermined height relative to the base. The proximal portion of the tubular element is of a configuration defined by the substantially planar base and an upper part that is generally ovoid. The base of the tubular element at the proximal portion is wider than at the distal end, to accommodate entry of surgical devices.

Other aspects of the invention involve methodology for utilization of an improved glottiscope system and apparatus of the type generally described.

These and other related objects, aspects and benefits of the invention disclosed herein will be better understood by reference to the following detailed description and the attached drawing figures.

BEST MODE FOR CARRYING OUT THE INVENTION

Figure 1:
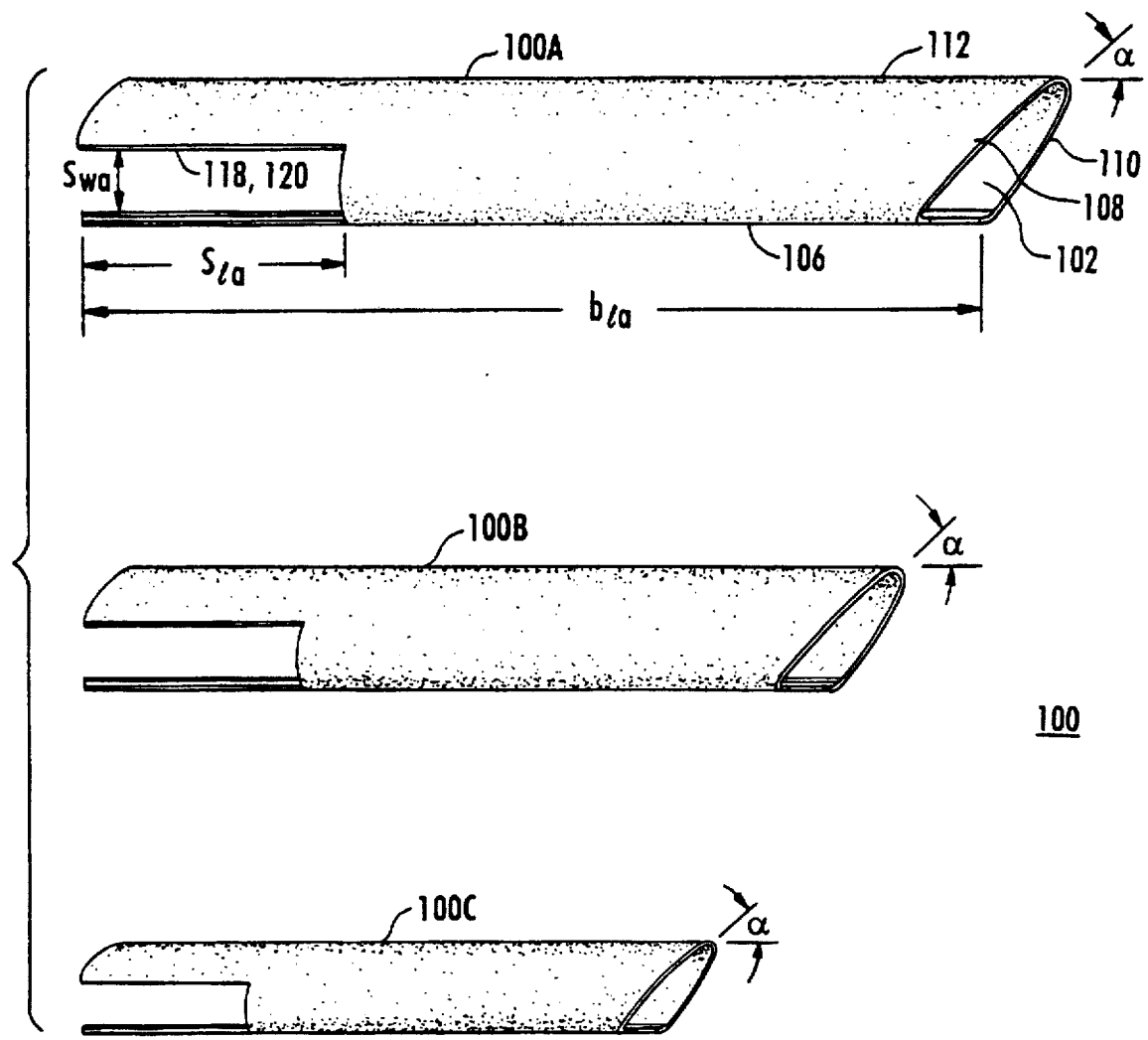
FIG. 1 is a side perspective view of a set of three tubular elements, of different dimensions but otherwise similar geometry, in accordance with the invention.

A modular glottiscope system according to an embodiment of the present invention employs, with consideration given to the patient's physical size, and with reference to FIG. 1, a set 100 of differently dimensioned elongate hollow tubular elements 100A–100C, at the distal end of each of which is an opening 102 defined by intersection of the tubular form shown with an imaginary plane. A routine longitudinal clamp-on light carrier (not shown) generally is used to provide illumination through the lumen of the glottiscope while it is being positioned with respect to the patient. It should be understood that other tubular elements intended to be part of the modular set will have the same geometry but be of different dimensions. What is the same for all the elongate tubular elements 100 of a given set 100 of such elements is that each is provided with a handle-attachment member 104 (not shown in FIG. 1; see FIGS. 8 and 9) of a standard shape and size to permit easily detachable attachment to a suitable handle (to be described later).

Figure 2:
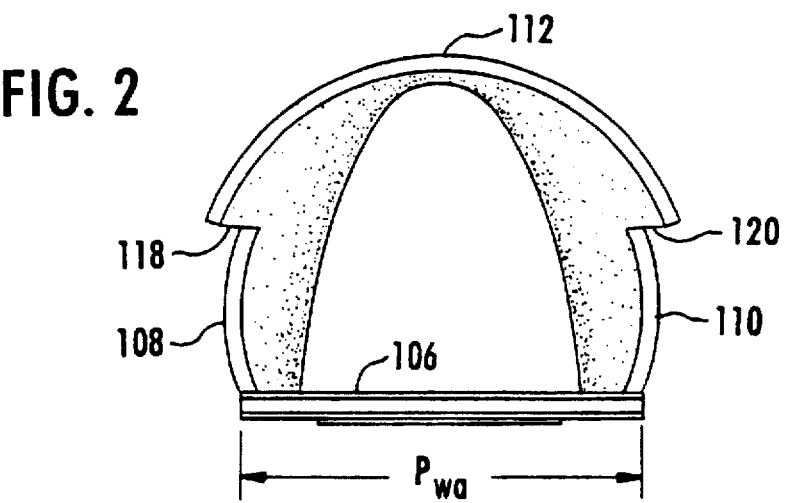
FIG. 2 is a transverse cross-sectional view at the proximal portion of the tubular element of FIG. 1.
Figure 3:
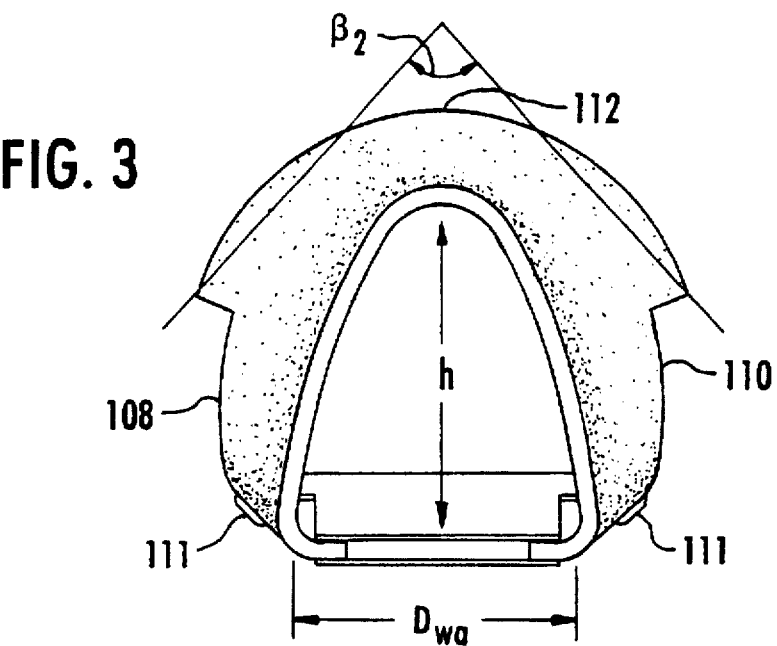
FIG. 3 is a transverse cross-sectional view at the distal portion of a tubular element of FIG. 1.

Each tubular element has a flat planar base 106, which can be detachable, of length "$b_{1a}$," a proximal width "$P_{wa}$" (FIG. 2) and a distal width "$D_{wa}$" (FIG. 3). Base 106 is smoothly contiguous with a pair of curved sides 108, 110 which intersect above at an apex line 112. The base 106 has opposite recessed sides that receive and mate with the corresponding inwardly extending ends of sides 108, 110, as best shown in FIG. 3, such that the base can be separated from element 100 by sliding the base rearward from the proximal end of the element. The base 106 is aligned longitudinally in the tubular element by internal extensions 111 that seat within corresponding recesses of sides 108, 110.

The respective intersections between curved sides 108 and 110 at apex line 112, of curved side 108 with planar base 106 at 114, and of curved side 110 with planar base 106 at 116, are all formed to have smoothly rounded outside surfaces to avoid inflicting unnecessary trauma to the patient's tissues. Similarly, where distal end opening 102 is defined by intersection of this complex triangular cross-section with an imaginary plane inclined at an angle "$\alpha$" to rounded apex 112, the opening edge is also smoothly rounded. A preferred range of $\alpha$ is 35°–70°. The goal is to avoid inflicting unnecessary trauma on the patient's tissue as the distal end, with opening 102 therein, is inserted into the patient's mouth and larynx.

Figure 6:
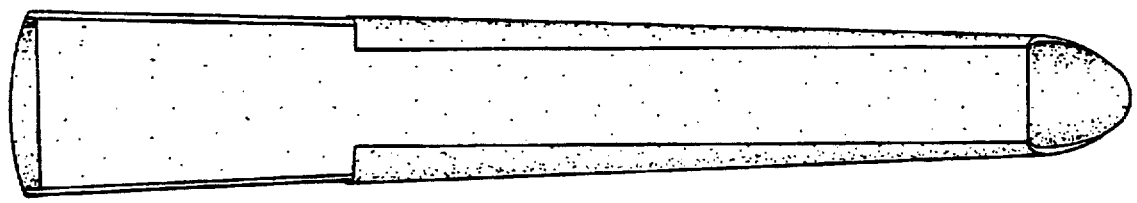
FIG. 6 is a bottom view of a larger tubular element with detachable flat planar base-plate shown in position.
Figure 7:
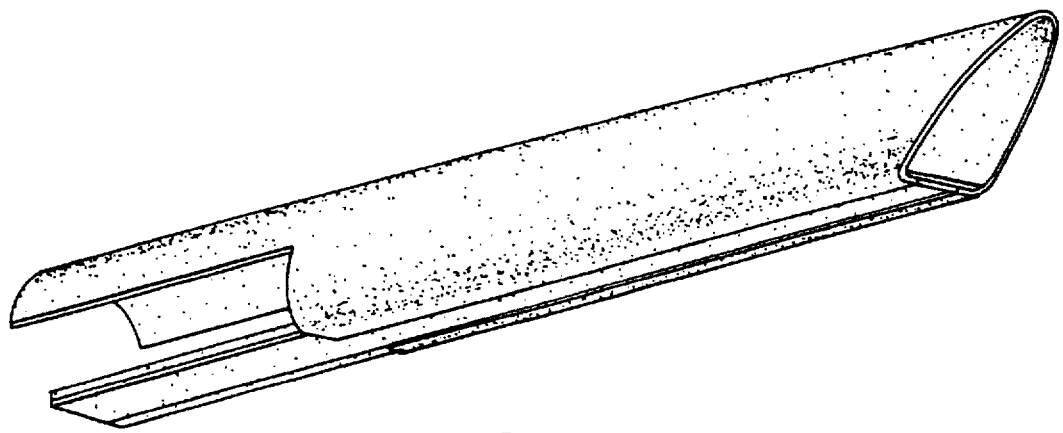
FIG. 7 is modified infra-lateral view of a tubular element.

At the proximal end of each tubular element 100, beneath handle attachment member 104 (FIGS. 8 and 9) and adjacent the base is provided a pair of laterally opposed slots 118 and 120, respectively formed in curved sides 108 and 110. The upper edges of slots 118 and 120 are preferably, but not necessarily, parallel to the planar base. The height of each of these slots, namely "$S_{wa}$", is selected to permit movement therein of the viewing and surgical operation tools which the surgeon expects to use. The length of slots 118 and 120, namely "$S_{la}$", likewise is chosen to suit the surgeon's needs. The width $P_{wa}$ of the proximal portion of the base 106 is greater than that ($D_{wa}$) at the distal end, to accommodate the surgeon's instruments. The width of base 106 may decrease gradually from the proximal to distal ends (FIG. 6).

An important advantage of the invented system is that it permits modularity and, based on actual measurements and/or the surgeon's experience, allows the surgeon to select the particular elongate tubular element 100A–C which will most effectively permit inspection and/or surgical treatment of that patient's glottal tissue. The surgeon has the freedom to select the most suitably sized and shaped tubular element and to readily and securely attach it, via its standardized handle-attachment member 104, to a standardized handle structure (to be described later). The surgeon thus can easily adjust to the needs of patients of differing anatomy, since it is intended that the set of elongate tubular elements 100 should include elements of all the necessary lengths and diameters, etc.

However, many surgical tools probably cannot be reduced in size indefinitely without adversely affecting their effectiveness. There may be a minimum size for the width and length of the parallel slots below which one may not go without adversely affecting the surgeon's ability to manipulate tools inserted longitudinally through that elongate tubular element by sideways lateral movement of parts of the tools in and out of the respective slots 118 and 120. The key is that the present system permits a considerable degree of flexibility to suit the instrumentation to the particularized needs of individual patients. If certain minor compromises have to be made, as just discussed, these still should not detract from the overall flexibility of the system in a laryngoscopic surgical practice.

As is also readily seen from FIG. 2, the proximal end portion of each elongate tubular element 100, immediately above the laterally opposed slots 118 and 120, is generally D-shaped in configuration with the form of a gently curved "inverted-U". Such a structure inherently possesses a degree of stiffness which, together with affixation to the preferably cylindrical handle-attachment member 104, provides sufficient rigidity and strength at the proximal end to permit the transfer of significant forces which must be applied in the course of surgery and treatment. In other words, the sizing and disposition of the slots to allow the residual portion of the tubular structure to have an inverted "U" form above for structural rigidity is deliberate and intended to ensure that the tubular element has sufficient inherent strength to perform all of its intended functions. Obviously, the thickness of the tubular element 100 and the choice of material from which it is made must also be taken into consideration in normal manner.

It is expected that after a particular surgical use the elongate tubular element 100 will be cleaned and sterilized, for subsequent reuse, which will be facilitated by the fact that the planar base separates from the upper arched segment of the tubular element.

This requires that the materials employed must be both tissue-compatible, i.e., capable of resisting any acidic substances (natural or medically applied), and capable of tolerating sterilization without adverse effect. There are numerous alloys and plastics available for such instruments, and stainless steel is a commonly preferred material. Any such known material, capable of providing the required strength, tissue compatibility and sterilization-tolerance, may be considered by persons of ordinary skill in the art to meet specific needs.

Figure 4:
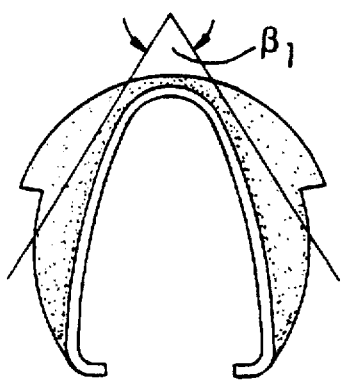
FIG. 4 is comparable to FIG. 3 for a smaller tubular element, with detachable flat planar base-plate removed.
Figure 5:
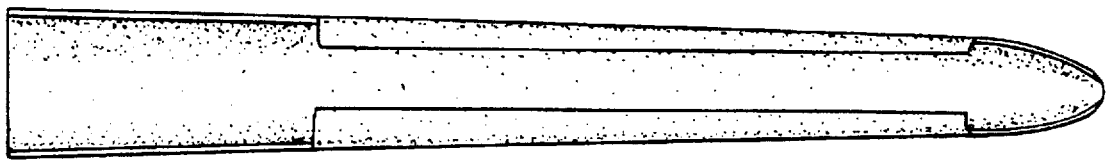
FIG. 5 is a bottom view of a tubular element, in accordance with one embodiment of the invention, with detachable flat planar base-plate removed.

As mentioned earlier, a key feature of the present system is that it has a high degree of modularity. This comprises not only selection of dimensions for tubular elements 100 but also in the curvatures and, therefore, the angle of intersection "$\beta_1$" between the curved sides 108 and 110, as seen in FIG. 4. This angle is determined between the two planes respectively tangent to the curved sides 108 and 110 at the apex line 112. Varying the height "h" for a given distal base width "DW" and/or varying the curvature of each of the sides 108, 110, may result in a different angle, i.e., "$\beta_2$" at the intersection of the curved sides at apex line 112 at the distal end of the tubular element. A preferred range of $\beta$ is 45°–120°. It may also permit variation in the width of the opposed slots, and thus the geometry of the space available to the surgeon to manipulate portions of surgical tools within the slots. Likewise, different sizing may be accomplished at the proximal end. In general, the base width at the proximal end, PW, will be greater than that at the distal end (DW).

As persons skilled in the art of mechanical design will readily appreciate, the curvature of each of the sides 108 and 110 need not be truly arcuate, namely sectors of a perfect circle. In fact, because the normal human glottis has a particular shape, it may be desirable to form the sides 108 and 110 so that there is a different local radius of curvature at different points between the base and the apex line. The sides of varying curvature with the portions close to apex line 112 at the distal end may be of a smaller radius of curvature than portions closer to base 106. This can be reversed, i.e., the sides 108 and 110 may be curved so that they have a smaller local radius of curvature closer to base 106 than they do close to apex line 112. The curvature of the upper part of the proximal end may be similarly varied. These are mere matters of choice and the modularity of the present system readily accommodates such variations so that the surgeon may have the greatest flexibility to meet the needs of individual patients and surgical operations.

Figure 8:
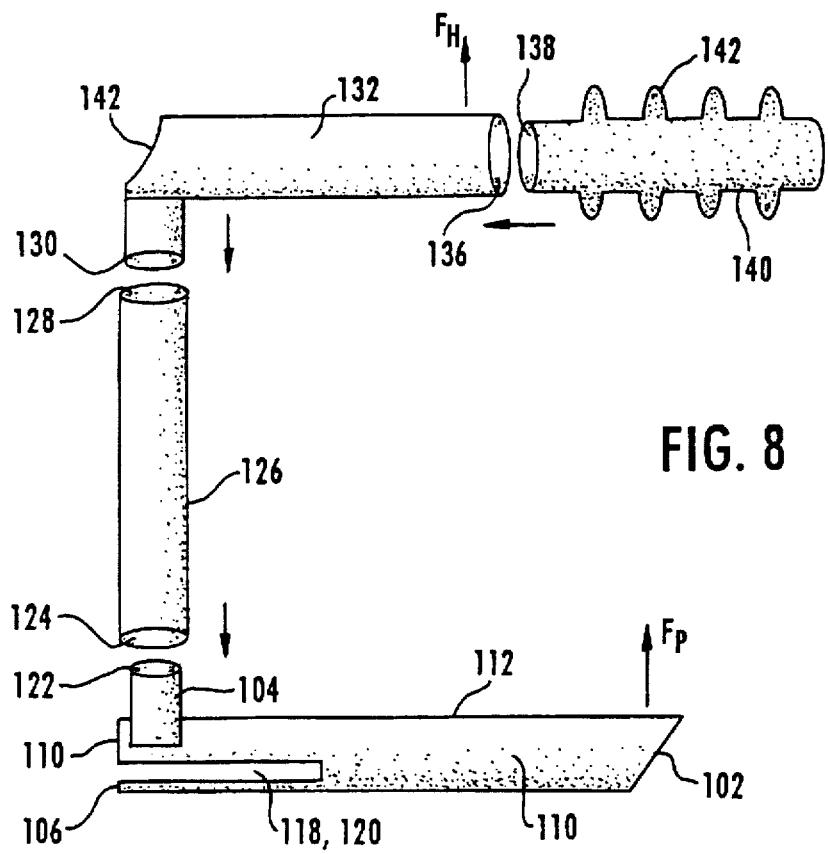
FIG. 8 is an exploded side elevation view of a modular glottiscope system with a simple handle and extension.

FIG. 8 is an exploded side view of certain basic components of a glottiscope according to a preferred embodiment of this invention. In this structure, which can be readily assembled, there is included a selected one of the elongate tubular elements 100 as described above. Handle-attachment member 104 may be readily made of the same material as tubular element 110 and may be welded, brazed, or otherwise affixed thereto. Over the distal end 122 of handle-attachment member 104 may be fitted a lower end 124 of an elongate tubular extension element 126. One of the modular aspects of the present invention is that such extension elements 126 may be provided in a variety of lengths, although each should preferably have a standardized inside diameter selected to closely fit to the standardized handle-attachment member 104. Into the opposite end 128 of extension element 126 may be inserted a short lateral connector part 130 of a generally "L" shaped handle 132. In the embodiment shown in FIG. 8, handle 132 has a first end 134 which may be closed off and be perpendicular to the longitudinal direction. Into a distal end opening 136 of handle 132 may be inserted a first end 138 of a handle extender element 140 which may be provided with an outer flexible cover having easy-to-grip ridges 142. In such a structure, what has hitherto been referred to as handle 132 may be considered an intermediate element between handle extender 140 and extension element 126 of the structure thus described.

Some surgeons may prefer to have extension element(s) 126 of other than a right cylindrical shape. Ergonomically suitable shapes for extension element 126 may be considered within the scope of this invention, e.g., having a central portion is made of irregular and/or larger cross-sectional size while both end portions are in the form of circular right cylinders made smoothly contiguous with the central portion.

It is intended that extension element 126 be securely fittable to handle-attachment member 104, that lateral portion 130 of handle 132 be securely fittable to the opposite end 128 of extension element 126, and that end 138 of handle extender 140 be securely fittable to end 136 of handle portion 132 easily. For reasons of scale, FIG. 8 does not show minor details of how the actual details of such a mechanism would appear. It is considered that persons of ordinary skill in the art will be aware of and be able to adapt any of numerous known structures and techniques for providing such secure but readily detachable attachments. Examples of such detachably attachable mechanisms include bayonet fittings, and as generally available in known systems for the same general purpose. The exact nature and form of such mechanisms is not critical to the present invention. All that is required is that various attachments be capable of easy and secure attachment and ready detachment as necessary for separate and effective sterilization of the various parts.

To facilitate the surgeon's activity, it is highly preferable to make extension element 126, handle portions 132 and 130, as well as handle extender 140 (if used), all of strong but relatively lightweight materials. Numerous alloys, composites, and other materials for such purposes are well-known to persons of ordinary skill in the art, and any of these may be selected as desired. The exact choice of materials is not considered critical for this invention, although it is preferred that the entire structure be relatively light. The key is that during use the surgeon may be expected to attach either handle portion 132 or handle extender 140, in any known manner, to an external suspension system and to manipulate the same to apply significant forces to the patient against the pull of gravity.

A smoothly curved corner surface is provided to handle 132 to provide ergonomic rest for the surgeon's thumb of the hand holding extension element 126 during manipulation of the glottiscope. In other words, a surgeon grasping handle portion 132 or handle extender 140 (if one is used) with one hand may grasp extension element 126 with his or her other hand while resting the thumb of that particular hand on the curved recess surface 142 for comfort and convenience.

Known suspension and fulcrum-holder systems for such equipment include, but are not necessarily limited to, the well-known Boston University Suspension System, the Loeb Laryngoscope Holder Support, and other "gallows"—type systems known in this art. This may require the addition of appropriately formed known elements to the components described hitherto. Such obvious modifications are considered well within the knowledge of persons of ordinary skill in the art, various elements of such systems are well-known and commercially available, and a detailed description thereof is therefore believed to be unnecessary and is omitted for conciseness.

Figure 9:
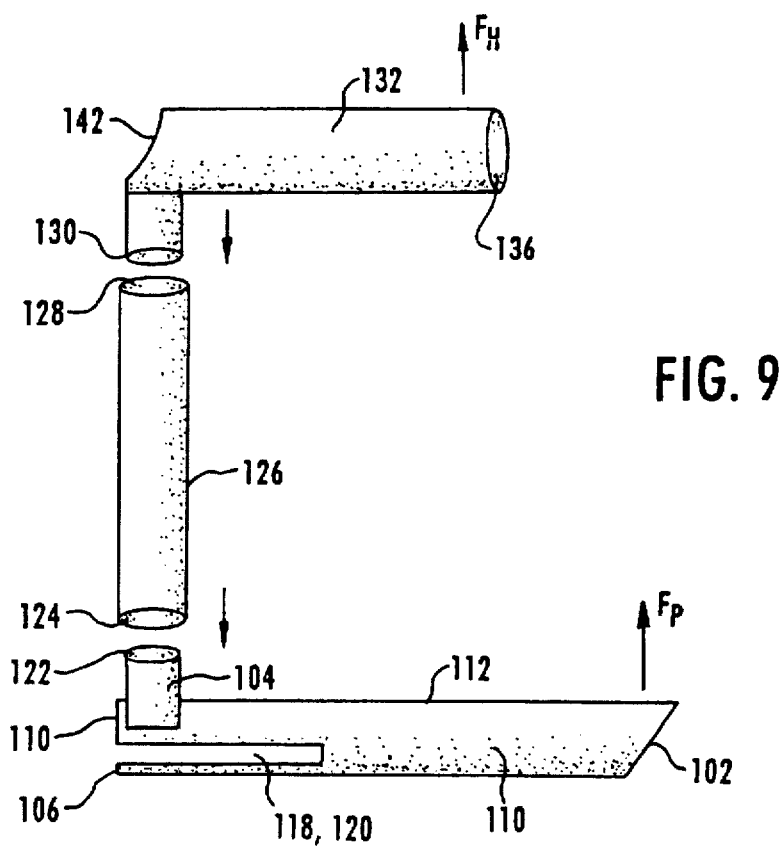
FIG. 9 is an exploded side elevation view of a variation of the glottiscope system according to this invention, in a form more particularly suitable for intubation for the administration of anesthesia to a patient.

As indicated in FIGS. 8 and 9 by bold arrows identified as "$F_H$" and "$F_P$", where a force "$F_H$" is applied by the surgeon via the handle structure, with tubular element 110 inserted into a patient's larynx, a consequential force "$F_P$" will be exerted on the patient. These forces can be significant, and a principal reason for choosing the depicted cross-section for tubular element 110, with curved sides coming together at a smoothly curved apex line, is to facilitate the application of such a force in a manner most advantageous for the surgeon without inflicting unnecessary trauma on the patient's tissues. Persons of ordinary skill in the art of performing laryngoscopic procedures will understand exactly how such forces are applied and why they are necessary to provide appropriate access to tissue to be treated.

The embodiment of FIG. 9 is particularly suitable for anesthesia applications in which a patient is intubated for the controlled provision of an anesthetic substance. In this modified structure, tubular element 100 may be exactly the same as described above, as is extension element 126 detachably attachable thereto at handle-attachment 104. The handle extender 140, described above with relation to FIG. 8, is omitted, and the extension element 126 may be used alone with the tubular element 110 (giving the assembled instrument a generally L-shape) or with the handle 132, extension element 126, and the tubular element 110 (giving the instrument a generally C-shape). For intubation purposes the surgeon will introduce an anesthetic-delivery endotracheal tube longitudinally through the tubular laryngoscope element 100 and out of end opening 102, through the vocal fold aperture and into the patient's trachea. Once this is satisfactorily done, the detachable planar base can be detached so that the upper portion of the glottiscope can be removed from the patient's throat without disturbing the endotracheal tube. This approach is invaluable in the difficult intubation such as is encountered with tumors that are obstructing the pharynx and/or larynx. Subsequently, an anesthetic substance, by itself or mixed with other substances, can be administered at a controlled rate for as long as needed. Similar intubation may be employed to suck out liquids from a patient's lungs through the trachea. Such obvious procedural modifications in the use of the hitherto described elements is expected to be well within the reach of persons of ordinary skill in the art.

When the system is to be employed for laryngoscopic/ glottiscopic procedures, the elongate tubular element 100 will be positioned in the larynx of a conveniently disposed patient with the outer surface of the base part of the element cross-section immediately adjacent the patient's upper teeth. This will ensure that the apex line is immediately adjacent the lower teeth of the patient, and this is particularly suitable, with appropriate choice of dimensions of the tubular element 100, for applying the distal end to the laryngeal tissue in the most advantageous manner.

Descriptions will now be provided of methods of using the above-disclosed universal glottiscope system for applications such as phonomicrosurgery and intubation for administration of anesthetic gases.

The performance of phonomicrosurgery on a particular patient will require an initial gross examination of the patient's oral cavity, larynx and pharynx, possibly with preliminary measurements, to determine the optimum dimensions and shape (determined by the apex angle and curvature distributions of the curved sides of the substantially triangular cross-section) for the patient. If the patient is a relatively small child, the surgeon may wish to select a tubular element 100 which has a somewhat more flared proximal end, e.g., to permit the use of a conventional microscope for viewing thereat. If the tubular element has been selected from a particular subset of a larger set of such elements, the surgeon may then select the appropriate universal handle system.

The patient will then be put in the most appropriate position for his or her needs, size, and comfort. U.S. Pat. No. 5,092,314, to Zeitels, in FIG. 4 and in its specification provides an explanation of how the well-known Boston University Suspension System may be utilized and the patient positioned in an exemplary application. These and other related portions of Zeitels are incorporated herein by reference as exemplars of what is known in this art. Once the patient is appropriately positioned, the surgeon will insert the distal end of the tubular element 100 into the patient's mouth and larynx, with the curved sides initially operatively disposed adjacent the patient's upper and lower teeth and with the apex line operatively disposed adjacent the patient's buccal mucosa. After the distal end of the tubular element 100 has passed the patient's circumvallate papilla at the origin of the tongue base, the tubular element must be rotated, e.g., counterclockwise, about 90°. The apex at the distal tip, where the apex line 112 ends at the top of opening 102, is then placed under the laryngeal surface of the epiglottis. At this time, the planar base of the tubular element 100 distracts the endotracheal tube posteriorly, between the arytenoids out of the surgical field, exposing the musculo-membranous vocal folds. The distal end is then advanced further to distract the false vocal folds laterally and to establish maximum exposure of the patient's true vocal folds.

It should be appreciated that the selected angle at the apex of the tubular element 100 most have been chosen to enable optimal lateral distraction of that particular patient's false vocal folds for exposure of a superior surface of the true vocal folds. When this is done appropriately, there will be available a very clear visualization of the patient's true vocal fold pathology. The surgeon can thereafter dispose suitable instruments, individually or simultaneously, longitudinally of the tubular element 100 to perform surgery on the musculo-membranous tissue of the patient's true vocal folds. In doing so, the surgeon will have the benefit of the pair of bilaterally opposed end slots 118 and 120 through which to manipulate proximal end portions of the viewing and/or surgical instruments more comfortably than was possible with the known structures of the kind which included only a single slot on one side.

Certain individuals may have anatomical characteristics which may create difficulties in the practice of conventional techniques for direct intubation, for example, for administration of anesthetic gases. It is also possible that even average individuals may have unique personal pathologies which might be unacceptably disturbed or traumatized during conventional intubation. This could complicate and perhaps even compromise subsequent endoscopic laryngeal procedures. The present invention provides a solution for such needs.

As described earlier with reference to the phonomicrosurgery procedure, the surgeon must initially decide on a suitable dimension and shape of an elongate tubular element 100 selected from a set thereof. One of the factors to be considered is the known and/or anticipated form of the patient's pathology. The patient is positioned so that either the cervical spine is in flexion with regard to the thoracic spine with the cranium in extension with regard to the cervical spine, or with the cranium in flexion with regard to the cervical spine. External counter-pressure may be applied manually to the patient's lower laryngeal cartilage framework. When the patient s glottal aperture and vocal fold pathology are adequately visualized with the glottiscope and its conventional lighting/optical devices attached longitudinally along the tubular element 100, the distal end of an endotracheal tube is gently passed through the glottal aperture and away from the vocal fold pathology. A conventional cuff provided at the end of the endotracheal tube is then inflated so that controlled flow of anesthetic gases can be administered to the patient. Since the connector at the proximal end of the endotracheal tube will not fit through the lumen of the glottiscope, the planar base plate 106 of the glottiscope is removed so that the gloltiscope separates into two segments, thus allowing for the upper portion of the tubular element to be removed from the throat without disturbing the endotracheal tube. This approach facilitates safely placing an orotracheal tube in a patient with obstructing throat pathology, however it may facilitate many other types of difficult intubations.

Obvious variations of these methods will no doubt occur to persons of ordinary skill in the art, e.g., surgeons and operating room staff, as the advantages of the structure disclosed herein become apparent through use, practice and shared experience.

As will be clear to persons of ordinary skill in the art, various types of known tools, devices and mechanisms can thus be readily used with the present invention for lighting, surgery, photography, suction, etc. as best suits the surgeon's or anesthesiologist's needs.

The fact that the surgeon or anesthesiologist has a variety of tubular elongate elements as taught in this invention facilitates precise accommodation of the laryngoscope to individual patient anatomy and lesion characteristics. The substantially triangular cross-section distally with the smooth apex line at a suitable angle between curved sides, facilitates a comfortable and effective fit of the distal end to the human glottis. The provision of two opposed slots at the proximal portion of the tubular element provides exceptional freedom for the surgeon to manipulate the proximal ends of elongate instruments, one or more at the same time, selectively introduce longitudinally of tubular element 100. For the smallest tubular elements, i.e., pediatric sizes, greater proximal widening of elongate tubular elements 100 may be necessary so that illumination from the surgical microscope (if one is used) does not reflect and cause glare off the edge of the proximal inner surface portion of the tube.

Although tubular elongate element 100 is shown in the drawing figures and is generally discussed above as being straight, there is no reason why it may not be made curved, the maximum benefits being realized by providing the above-described substantially triangular uniform cross-section with curved sides, the bilaterally opposed proximal slots, and the standardized handle-attachment at the proximal end.

Although the present invention has been described and illustrated in detail, it should be clearly understood that the same is by way of illustration and example only and is not to be taken by way of limitation, the spirit and scope of the present invention being limited only by the terms of the appended claims.

I claim:

1. A modular glottiscope system, comprising:
   a plurality of elongate tubular elements of respectively different counterpart dimensions, wherein each tubular element has a distal end to be inserted into a patient's larynx and a proximal end via which one or more surgical devices may be inserted operatively, and a pair of curved sides joining with a substantially planar base
   wherein a distal portion of each tubular element has a generally triangular cross-section defined by the substantially planar base of predetermined width and length and the pair of curved sides intersecting at a predetermined first angle at an apex line at a predetermined first height relative to the base,
   wherein proximal end portions of the two curved sides are provided with respective slots, each of a predetermined width and length, intermediate the base and the apex line and starting at a predetermined second height relative to the base, and
   wherein a standardized handle-attachment member is affixed adjacent the proximal end; and
   a handle attachable to the standardized handle-attachment member of any of the elongate tubular elements.

2. The system according to claim 1, wherein said base is configured to be attachable from said pair of curved sides.

3. The system according to claim 1, wherein a proximal portion of each tubular element has an upper part that is ovoid in configuration and the substantially flat base of width greater than that at the distal portion of said tubular element.

4. The system according to claim 1, wherein the width of said tubular element transitions gradually between proximal and distal ends of said tubular element.

5. The system according to claim 1, wherein the distal end has an opening defined by an intersection between the cross-section and a plane inclined at a second angle to the planar base.

6. The system according to claim 1, wherein each of the tubular elements is made of a tissue-compatible material.

7. The system according to claim 1, wherein:
   the handle comprises an extension element having a first end attachable at the standardized handle-attachment member of any of the elongate tubular elements and a second end provided with an attachment fitting, and
   a second element having a first end formed to securely fit to the attachment fitting of the extension element,
   and wherein, when the handle is attached via the extension element to any one of the elongate tubular elements, the extension element is substantially perpendicular to the apex line and the second element fixed to the extension element is parallel to the apex line.

8. The system according to claim 7, wherein:
   the second element comprises a handle extender and an intermediate part affixable at a first end to the attachment fitting of the extension element and at a second end to the handle extender.

9. The system according to claim 1, wherein:
the curved sides of each tubular element are symmetrical and have a varying radius of curvature between the base and the apex line.

10. The system according to claim 9, wherein:
the radius of curvature varies from a maximum value adjacent the base to a minimum value between the base and the apex line.

11. The system according to claim 9, wherein:
the radius of curvature varies from a minimum value adjacent the base to a maximum value between the base and the apex line.

12. The system according to claim 9, wherein:
the intersection between the curved sides at the apex line and intersections between each of the curved sides and the base are each formed with a local small radius of curvature to provide smoothly rounded external surfaces free of sharp edges.

13. The system according to claim 1, wherein:
a substantial portion of the handle is made hollow to reduce the weight thereof.

14. The system according to claim 1, further comprising:
adjustable support means connectable to the handle to apply thereto a biasing force whereby a corresponding patient-support force is applied by the tubular element to a patient under treatment.

15. The system according to claim 1, wherein:
the plurality of elongate tubular elements are formed as a plurality of sets, the tubular elements of each set having a respective standardized handle-attachment attachable only to a corresponding respective handle.

16. The system according to claim 1, wherein:
the handle, when attached to a selected one of the plurality of tubular elements, is oriented substantially parallel to the apex line of the tubular element.

17. The system according to claim 1, wherein:
the first angle is in a range 45° to 120°.

18. The system according to claim 5, wherein:
the second angle is in a range 35° to 70°.

19. The system according to claim 18, wherein:
the first angle is in a range 45° to 120°.

20. The laryngoscope system of claim 1, wherein said dimensions are matched to dimensions of the oral cavity, oropharynx and larynx of patients.

21. An improved laryngoscope comprising:
an elongate tubular element having arcuate opposite sides joined by a substantially planar base, a distal end of said element to be inserted into a patient's larynx and a proximal end of said element for receiving one or more surgical devices individually or simultaneously, and having a handle attachable to a proximal end portion of the tubular element, wherein:
a distal portion of the tubular element is of a uniform generally triangular cross-section defined by a substantially planar base and a pair of curved sides intersecting at a predetermined first angle at an apex line at a predetermined height relative to the base; and
a proximal portion of the tubular element is of a cross-section defined by said substantially planar base and an upper part that is generally ovoid in configuration, the base being wider at said proximal portion than at said distal portion.

22. The laryngoscope according to claim 21, wherein said base is configured to be manually detachable from each element sides.

23. The laryngoscope according to claim 21, further comprising:
a handle attachment provided at the tubular element adjacent the proximal end thereof, for secure but manually detachable attachment of the handle thereat.

24. The laryngoscope of claim 23, wherein opposite sides of the tubular element are formed with slots extending to the proximal end.

25. A method of accessing a patient's vocal folds for selective viewing and treatment thereof, using a modular glottiscope system that comprises a plurality of elongate tubular elements of respectively different counterpart dimensions matchable to dimensions of the oral cavity, oropharynx and larynx of a patient, wherein each tubular element has a distal generally triangular uniform cross-section defined by a substantially planar base of predetermined width and length and a pair of curved sides intersecting at a predetermined angle at an apex line at a predetermined height relative to the base, and further wherein proximal end portions of the two curved sides of the tubular element are each provided with a respective opposed slot, each slot being of predetermined width and length, intermediate to the base and the apex line and at a predetermined separation relative to the base, the method comprising:
inserting into the patient's oral cavity a distal end portion of a selected tubular element of the laryngoscope system matched to that patient to a position close to the patient's vocal folds;
selecting dimensions of the selected tubular element to match dimensions of the oral cavity and larynx of the patient from the set of tubular elements having respective dimensions within predetermined ranges, with each of the tubular elements having adjacent a proximal end a standardized handle-attachment member attachable to a standardized handle; and
after the distal end of the tubular element has been inserted past the circumvallate papilla at the origin of the patient's tongue base, rotating the tubular element about 90° so that a distal end of the apex line is placed under the laryngeal surface of the epiglottis;
disposing the base of the glottiscope adjacent to the patient's upper teeth with the apex line operatively disposed adjacent to the patient's lower teeth; and
advancing the distal end of the tubular element to distract the patient's false vocal folds for exposure of a superior surface of the vocal folds, to thereby improve visualization of vocal fold pathology and to provide optimal visualization of the musculo-membranous tissue of the patient's vocal folds in a manner such that pathological tissue is not disrupted;
utilizing the proximal lateral slots to facilitate angulation of hand instruments, which are placed within the lumen of the tubular element to retract tissue for viewing and treating the patient's vocal folds.

26. A method of performing phonomicrosurgery on a patient, comprising the steps of:
inserting, through the patient's oral cavity and oropharynx, a distal end portion of a tubular element of a laryngoscope, wherein
(a) the tubular element has a distal substantially triangular uniform cross-section defined by a substantially planar base of predetermined width and length and a pair of curved sides intersecting at a predetermined angle at an apex line at a predetermined height relative to the base;

(b) the predetermined angle at the apex is selected to enable a lateral distraction of the patient's false vocal folds for exposure of a superior surface of the vocal folds, to thereby improve visualization of vocal fold pathology and to provide space for a user to dispose instruments via the tubular element for surgery of musculo-membranous tissue of the patient's vocal folds;

(c) dimensions of the tubular element are selected to match dimensions of the oral cavity, oropharynx and larynx of the patient from a set of tubular elements having respective dimensions within predetermined ranges, with each of the tubular elements having, adjacent a proximal end, a standardized handle-attachment element attached to a standardized handle;

(d) an extension piece of the handle being supported by a suspension gallows or fulcrum laryngoscope holder;

(e) a surgical microscope providing magnification and illumination of the glottal surgical field; and (f) lateral slots of the proximal end of the tubular element allowing for optimal retraction of a pathological lesion and the normal layered microstructural tissue of the vocal fold without obscuring the surgeon's visualization through the microscope.

27. A method of intubating a patient, comprising the steps of:

inserting, through the patient's oral cavity and oropharynx, a distal end portion of a tubular element of a laryngoscope, wherein (a) the tubular element: has a distal substantially triangular uniform cross-section defined by a substantially planar base of predetermined width and length and a pair of curved sides intersecting at a predetermined angle at an apex line at a predetermined height relative to the base, (b) the predetermined angle at the apex is selected to enable a lateral distraction of the patient's false vocal folds for exposure of a superior surface of the vocal folds, to thereby improve visualization of vocal fold pathology and to avoid trauma to these abnormal tissues, (c) dimensions of the tubular element are selected to match dimensions of the oral cavity, oropharynx and larynx of the patient from a set of tubular elements having respective dimensions within predetermined ranges, with each of the tubular elements having, adjacent a proximal end, a standardized handle-attachment element attached to a standardized handle, (d) the curved sides of the tubular element are initially disposed adjacent the patient's upper and lower teeth and the apex line is disposed adjacent the patient's buccal mucosa;

after the distal end of the tubular element has been inserted past the circumvallate papilla at the origin of the patient's tongue base, rotating the tubular element about 90° so that a distal end of the apex line is placed under the laryngeal surface of the epiglottis, (e) the distal end of the tubular element is advanced to enable the lateral distraction of the patient's false vocal folds for exposure of a superior surface of the vocal folds, to thereby improve visualization of vocal fold pathology and to provide visualization of the musculo-membranous tissue of the patient's vocal folds in a manner such that pathological tissue is not disrupted during intubation, (f) the distal end of an endotracheal tube with an inflatable cuff is passed through the tubular element of the glottiscope , and subsequently through the vocal fold aperture into the trachea, and the cuff is inflated, and (g) the planar base of the glottiscope is retracted proximally so that the glottiscope can be removed from the patient without disturbing the endotracheal tube.

* * * * *